United States Patent [19]

Dickson et al.

[11] Patent Number: 5,482,848
[45] Date of Patent: Jan. 9, 1996

[54] MATRIX-DEGRADING METALLOPROTEINASE

[75] Inventors: Robert B. Dickson, Silver Spring, Md.; Yuenian E. Shi, Roslyn Heights, N.Y.

[73] Assignee: Georgetown University, Washington, D.C.

[21] Appl. No.: 199,792

[22] Filed: Feb. 22, 1994

Related U.S. Application Data

[63] Continuation-in-part of Ser. No. 936,512, Aug. 28, 1992, abandoned.

[51] Int. Cl.⁶ ............................. C12N 9/50; C12N 9/96
[52] U.S. Cl. .................... 435/219; 435/188; 435/226; 424/94.1; 424/94.67
[58] Field of Search ..................... 435/23, 7.23, 7.4, 435/226, 188, 219; 424/94.1, 94.67

[56] References Cited

FOREIGN PATENT DOCUMENTS 9010062  9/1990  WIPO .

OTHER PUBLICATIONS

Van Den Bruce F., Genes Involved In Tumor Invasion ... Int J Cancer 52 653–657 1992.

*Primary Examiner*—William H. Beisner
*Assistant Examiner*—Ralph Gitomer
*Attorney, Agent, or Firm*—Glenna Hendricks; Stephen Gates; Carol Tracy

[57] ABSTRACT

An 80 kDa metaloproteinase is found in hormone-dependent human breast cancer cells. The enzyme is active in the presence of calcium, manganese, or magnesium ions. The 80 kDa proteinase is useful for evaluating therapeutic progress and in formulating plans for treatment.

6 Claims, No Drawings

MATRIX-DEGRADING METALLOPROTEINASE

This application is a continuation-in-part of U.S. Ser. No. 07/936,512, filed Aug. 28, 1992, now abandoned.

FIELD OF THE INVENTION

This invention pertains to an 80 kDa metalloproteinase and antibodies thereto useful for evaluating and treating breast cancer.

BACKGROUND OF THE INVENTION

The capacity of cancer cells to metastasize and invade tissue is facilitated by degradation of the basement membrane (BM). Several protease enzymes have been shown to facilitate the process of invasion of tumor cells. One family of enzymes known as matrix metalloproteinases (MMP) has been implicated as enhancing the degradation of the basement membrane to allow tumorous cells to invade tissues. MMP's differ in molecular weight and in their antigenic properties. Two major metalloproteinases studied previously had molecular weights of about 70 kDa and 92 kDa. Both of these MMP's have been shown to enhance ability of tumor cells to metastasize. Two natural inhibitors of these enzymes known as tissue inhibitors of metalloproteinase (TIMP) have been identified. The inactivated, unclipped collagenases are generally secreted as a complex with TIMP. Enzymic activity of the 72 kDa and 92 kDa depends on secreted ratios of collagenase/TIMP and the activational process. Methods of measuring 72 kDA and 92 kDa collagenase breast cancer are being used to develop useful prognostic indicators.

Fully metastatic models of hormone-responsive breast cancer have only recently been described, and some progress has been made in studying in vitro invasion systems to evaluate regulatory mechanisms. The reconstituted basement membrane extract, Matrigel, has been utilized in assessing invasive potential of cancer cells. Invasion of hormone-dependent breast cancer cells in vitro is stimulated by estrogen or tamoxifin (a weakly estrogenic, nonsteroidal antiestrogen) but not by the steroidal pure antiestrogen ICI 164,384.

Recently a synthetic low-molecular-weight MMP inhibitor, [4-(N-hydroxyamino)-2R-isobutyl-3S-(thiopen- 2-ylthiomethyl)succinyl]-L-phenylalanine-N-methylamide (BB-94) has been identified which has been shown to be effective in treatment of ovarian malignancies and in some forms of breast cancer. That agent seems to be effective against both the 72 kDa and 92 kDa metalloproteinases. However, both BB-94 and TIMP's have now been shown to lack inhibitory effect on the metalloproteinase of the invention.

Various proteinases have been identified by zymography on gelatin-containing gels.

SUMMARY OF THE INVENTION

The present invention is a metalloproteinase having a molecular weight of about 80 kDa which is present in hormone-dependent human breast cancer cells. The enzyme is active in the presence of calcium, manganese or magnesium ions. The invention provides methods for detection of the 80 kDa proteinase and methods of formulating treatment methodologies and of evaluating therapeutic progress by measuring the presence of the 80 kDa proteinase in the patient.

The presence of the 80 kDa proteinase may be detected directly by analysis of tumor tissue or indirectly by immunological means. Hence, methods disclosed herein have value in monitoring factors related to the metastatic process and in assessing effectiveness of response to treatment methodologies. Furthermore, since it has been shown that agents used in treatment to inhibit proteinase activity frequently are quite specific in their activity, it is necessary to evaluate effectiveness of any agent on the particular proteinases produced in the patient, since treatment with an inappropriate inhibitor can be both ineffective and costly.

DETAILED DESCRIPTION OF THE INVENTION

The novel matrix-degrading enzyme of the invention was identified from human breast cancer cells. The enzyme appears as a major gelatinase in hormone-dependent breast cancer cells lines, The 80 kDa metalloproteinase that degrades type IV collagen appears to play a significant role in metastases of breast cancer, particularly hormone dependent breast cancer. The 80 kDa MMP represents a major component of gelatin-degrading proteases in hormone-dependent human breast cancer cells. The 80 kDa protease (1) is active in the presence of $Ca^2$, $Mg^2$ and $Mn^2$, (2) is active over a pH range of 7.5 to 9.5 with an optimum at about pH 8.5, (3) is not activated by p-aminophenylmercuric and (4) degrades gelatin and type IV collagen. The enzyme is inhibited by EDTA and leupeptin.

The 80 kDa proteinase of the invention differs from the previously known 72 kDa and 92 kDa type IV collagenases which also degrade type IV collagen. For example, neither of those prior art proteinases are activated by the $Mn^2$ ion. Furthermore, the 72 kDa and 92 kDa proteinases exhibit peak activity in the neutral pH range. They are most prominently present in tumors that are not hormone dependent. The drug BB-94 appears to be effective against malignancies which are not hormone-dependent, but not against malignancies that are hormone dependent. Hence, the identification of the particular MMP's produced is important in constructing treatment protocols. The novel enzyme of the invention is not inhibited by tissue inhibitor of prior art metalloproteinases.

The 80 kDa protease may be used to generate antibodies against the enzyme by methods commonly used in the art. U.S. Pat. Nos. 4, 151,268, 4,197,237 and 4,123,431, which are incorporated herein by reference, disclose some of the known means of producing such antibodies. For detection purposes, antibodies may be labeled by methods known in the art. For example, U.S. Pat. No. 4,302,438, which is incorporated herein by reference, describes tritium labeling procedure.

To isolate and characterize the 80 kDa gelatinolytic enzyme, 2.5 liters of the serum-free conditioned medium (CM) with T47Dco cells were concentrated 100 fold by ultrafiltration. The concentrated CM was first applied to a gelatin-Sepharose column. Unexpectedly, the 80 kDa gelatinolytic activity was detected in the flow-through fractions. The 92 and 72 kDa gelatinases are absorbed by gelatin-Sepharose, and can be eluted therefrom with $Me_2SO$. When the gelatin-Sepharose exposed to T47Dco conditioned medium was then subjected to standard elution with $Me_2SO$, 92 kDa and 72 kDa gelatinases were eluted. The gelatin-Sepharose flow-through (prior to $Me_2SO_4$ elution) is now used as the first step in separation of the 80 kDa gelatinase from other gelatinases which have an affinity for gelatin-Sepharose. Subsequent purifications were conducted using Con A and magnesium, manganese, and zinc ions in chelation chromatography. The specific activity of the recovery of enzyme activity against gelatin is shown in Table I. There was decrease in the total enzymatic activity after gelatin affinity chromatography which indicates the removal of some gelatin-binding gelatinases. After $Zn^{2+}$ chelation chromatography, approximately 85-fold increase in specific activity was achieved.

TABLE I

| Purification step | total protein[a] | Total Activity[b] | Specific Activity[c] | Purification | Recovery (%) |
|---|---|---|---|---|---|
| Concentrated medium | 84 | 11,234 | 133 | | |
| Gelatin-Sepharose flow-through | 79 | 1,522 | 19 | 1 | 100[d] |
| Con A-Sepharose | 3.9 | 412 | 105 | 5.5 | 27 |
| $Zn^{2+}$ chelation | 0.136 | 221 | 1,625 | 85 | 16 |

[a] $A_{280}$ (mg)
[b] Units wherein one unit activity is defined as 1000 dpm of soluble gelatin (total soluble count subtracted with background count) in 20 µl pooled active fraction
[c] Units/mg wherein specific activity was calculated by dividing total activity by total protein.
[d] 92 kDa and 72 kDa collagenases and other gelatinase were removed by gelatin Sepharose. Thus the activity of the gelatin Sepharose flow-through sample represents the 80 kDa enzyme.

The 80 kDa enzyme has now been further purified using two additional reverse phase HPLC steps to apparent homogeneity. The protein was then cleaved to yield several large, detectable peptides using cyanogen bromide treatment.

Materials and Methods

Reagents:

The protease inhibitors phenylmethylsulfonyl fluoride, leupeptin and peptstatin were obtained from Boehringer Manneheim, Indianapolis, Indiana. EDTA, benzaminidine, dithiothreitol, type I collagen, and iodoactamide were obtained from Signma, St. Louis, Mo. Type I $^3$H-collagen was obtained from Dupont, Wilmington, Del. Recombinant 72 kDa type IV collagenase, recombinant TIMP-2 and type IV $^3$H-collagen were provided by Molecular Oncology, Inc., Gaithersburg, Md. Transferrin, laminin and fibronectin were purchased from Collaborative Research. Gelatin,-Sepharose and chelate-Sepharose were from Pharmacia, Piscataway, N.J.

Cell Lines and Culture Conditions:

T47Dco cells were provided by Dr. Edwards of the University of Colorado. MCF-7 cells were obtained from Dr. Marvin Rich of the Michigan Cancer Foundation, and MDA-MB-435 was supplied by Janet Price of the University of Tex. M. D. Anderson Cancer Center, Houston, Tex. All other breast cancer cell lines were obtained from the American Type culture Collection, Rockville, Md. All cells lines were maintained in Costar T75 flasks in Richters IM EM (Biofluides, Rockville, Md.) supplemented with 10% fetal calf serum (GABCO, New York N.Y.).

Preparation of Conditioned Medium and Plasma Membranes:

In order to remove the soluble gelatinases present in the serum, subconfluent monolayers obtained by culturing the cells for three days in improved minimum essential medium (IMEM) supplemented with 10% fetal calf serum that was previously exposed to gelatin affinity chromatography. The medium was discarded and the monolayers were washed twice with phosphate-buffered saline. The monolayers were cultured in the absence of serum, in IMEM supplemented with transferrin (1 mg/liter), fibronectin (1 mg/liter) and trace elements. After 24 hours, the serum-free medium was discarded, and the cells were replenished with the fresh serum-free medium and cultured for another 48 hours. At the end of this period, the conditioned medium was collected The medium was then centrifuged at 12×g, and supernatants were saved and concentrated 20 fold by ultrafiltration using Centripreps (Amicon Division, Molecular weight cutoff, 10,000) at 4° C. Isolation of plasma membrane from tumors was performed by homogenizing the tissue with phosphate-buffered saline containing 1 mM PMSF and 1 mM benzamidine. After centrifugation at low speed (800×g) for 15 minutes, the supernatant was further centrifuged at 100,000×g for one hour. The membrane pellet was extracted overnight at 4° C. in a 4 mM Tris (pH 7.4) buffer containing 200 mM NaCl, 1 mM PMSF, 1 mM benzamidine, and 2% Triton X-100.

Gelatin-Sepharose Chromatography:

The 80 kDa protease from T47Dco cells was first separated from other minor gelatinases by virtue of its lack of affinity for gelatin-Sepharose chromatography. This was accomplished by passing the concentrated condition medium over a column (1.5×4 cm) of gelatin-Sepharose equilibrated with collagenase buffer (buffer C) containing 50 mM Tris (pH 7.5), 0.15 mM NaCl 5 mM $Ca^{2+}$, and 0.05% Brij-35. When the column flow-through sample was tested on gelatin zymography, no detectable 92 kDa or 72 kDa gelatinases were observed. Therefore, this gelatin-Sepharose flow-through sample was considered as the "starting material" for subsequent purification.

Con A-Sepharose:

The concentrated condition medium depleted of 92 and 72 kDa gelatinases was applied to a Con A column (1.5×4.5 cm) equilibrated with buffer C. The column was washed with free column volumes of this buffer. Adsorbed proteins were eluted with 2 column volumes of buffer C containing 0.1M methyl mannopyranose (Sigma) and 3 column volumes of buffer C containing 5M methyl mannosylpyranoside.

Zinc Chelation Sepharose Chromatography:

The zinc chelation Sepharose column was prepared by passing 20 ml of 30 mM $ZnCl_2$ though a column (1.5×5 cm) of chelate-Sepharose. The active fractions from the above Con A column were pooled, dialyzed against buffer C without $Ca^{2+}$ and passed over the column equilibrated with buffer C without $Ca^{2+}$. The column was eluted as previously described.

Substrate Zymograms:

Preparation of substrate gels and subsequent detection of proteolytic activity were conducted as previously described according to the methods of Heussen, et al. (Anal. Biochem, 103: 196–202, 1980). Protease substrates utilized were gelatin (1 mg/ml). Preparation of substrate gels was carried out in Laemmli buffer system except that the amount of ammonium sulfate was doubled. Proteins were first separated by electrophoresis on a 10% polyacrylamide gel containing different substrates without reducing agent. The electrophoresis was performed at 4° C. at constant current of 40 mA. the gel was washed three times for 20 minutes in 50 mM Tris buffer (pH 7.5) containing 5 mM $Ca^{2+}$, 150 mM NaCl and 2.5% Triton X-100. After overnight incubation at 37° C., the gels were stained with 0.25% Coomassie blue in 5% acetic acid and 30% methanol for 1 hour and destained with the same buffer. Proteolytic activities were detected by clear zones indicating the lysis of the substrate.

Enzymatic Degradation Assay:

Enzymatic activity was assayed by measuring degradation of $^3$H-gelatin in a manner conceptually similar to that of Stetler-Stevenson ((Biochemistry, 31: 1665–1672 (1992)) with some minor but critical modifications. Tritated type I collagen (NEN) was diluted with nonradioactive type I collagen and then denatured at 55° C. for 10 minutes. Enzyme samples and gelatin were added to buffer C to a final volume of 55 µl. After overnight incubation at 37° C., the reaction was stopped by addition of EDTA at a final concentration of 18 mM. Proteins were precipitated on ice with 0.3% of trichloroacetic acid and 0.0014% of tannic acid, The radioactive soluble peptide fragments were detected in a liquid scintillation counter. The critical modification of the procedure for detection of 80 kDa enzyme in this soluble assay was the very low concentration of trichloroacetic acid in the final precipitation step. When the final concentration of trichloroacetic acid is increased to 1%, the apparent enzymatic activity of the 80 kDa protease (determined by soluble counts) decreased dramatically.

The enzymatic activity of 80 kDa against type IV collagen was also evaluated in soluble reaction mixture containing type IV $^3$H collagen and 80 kDa in the buffer C. After overnight incubation at 37° C., degradation of the type IV collagen was analyzed by DSD-Page followed by autoradiography.

Determination of Optimal pH range:

Optimal pH range was determined by incubating slices of gel (each corresponding to one lane) in Hank's balanced salt solution adjusted to pH values of 5, 6, 7, 8, 9 and 10. After an overnight incubation in separate dishes at 37° C. with shaking the pH values of the Hank's balanced salt solution were measured again to ensure that the pH values had not been changed.

Responses to Inhibitors:

Inhibitors were evaluated in gelatin substrate zymography. TIMP-2 was subjected to the soluble gelatin degradation assay. Aliquots of partially purified 80 kDa protease and 72 kDa gelatinase were subjected to gelatin zymography. In order to allow the inhibitors to diffuse sufficiently into the gel following electrophoresis, the gels were washed three times (10 minutes/wash) with cold 2.5% Triton X-100 buffer and sliced into individual lanes. Each slice was incubated with protease inhibitor at 4° C. for two hours. Samples were then incubated at 37° C. overnight. Inhibition of gelatin-degrading activities of the proteases were evaluated by the loss of the zone of degradation seen on zymography compared to that of the untreated sample.

The properties of the 80 kDa gelatinase was compared to the prior art 72 kDa and 92 kDa gelatinases. Mammalian metalloproteinases generally possess consensus metal ion-binding sites, termed the "zinc-binding site". Operationally, calcium as well as zinc is used to study the proteolytic activity of enzymes. While the 80 kDa enzyme can also utilize 5 mM $Ca^{2+}$ to yield maximal activity. EDTA at 5 mM inhibited the activity of all three gelatinases. In contrast to the 92 kDa and 72 kDa gelatinases which only utilized calcium, the 80 kDa protease could also utilize magnesium and manganese ions.

To further confirm that the blocking effect of EDTA on gelatinolytic activity on the 80 kDa gelatinase is due to its metal-chelation activity, a reversibility assay was carried out. It was found that as little as 0.5 mM EDTA totally blocked the gelatinolytic activity of all three gelatinases. This inhibitory effect of the EDTA on the gelatinolytic activity of 80 kDa gelatinase was completely reversed by 5 mM calcium, magnesium, or manganese ion.

The 80 kDa protease was active when the samples were incubated at room temperature or at 55° C. for 25 minutes. The activity was lost dramatically after heating the 80 kDa enzyme at 100° C. for 5 minutes. No activity of the 80 kDa enzyme was observed after heating at 100° C. for it minutes.

Detection of 80 kDa Matrix-Degrading Proteinase in Breast Tumors:

Tumor tissue obtained by biopsy is homogenized and the nuclei and connective tissue remnants are removed by centrifugation at 800×g for 30 minutes. After further centrifugation at 100,000×g for one hour, a crude membrane pellet is obtained. The pellet was extracted overnight at 4° C. in a 4 mM Tris buffer (pH 7.5) containing 200 mM NaCl, 1 mM PMSF, 1 mM benzamidine, and 2% Triton X-100 in accord with the methods described above. The resulting material is subjected to Gelatin-Sepharose chromatography as described above. The flowthrough sample is subjected to gelatin to determine whether 80 kDa gelatinase is present. (It is then possible to elute the column with $Me_2SO$ for extraction of 92 kDa and 72 kDa gelatinases.)

Further confirmation of the identity of 80 kDa proteinase may be carried out by chelation in accord with the description of zinc chelation suggested above. It is also possible to chelate using calcium, magnesium or manganese for dialysis.

Since 72 kDa and 92 kDa are responsive to inhibitors that are not effective against 80 kDa, it is necessary to identify whether or not a particular tumor produces the 80 kDa protease. This is especially true as drugs such as BB-94 come on the market. In the case of BB-94, the patient who has a tumor producing primarily the 80 kDa metalloprotease would probably not benefit greatly from treatment with that agent. Ineffective treatment leads to loss of precious time in formulating an appropriate treatment plan. For this reason, it would be advantageous to perform diagnostic test on all breast cancer tissue for presence of 80 kDa proteinase.

Antibodies may also be made against the 80 kDa proteinase by known methods.

Monoclonal and Polyclonal Antibodies:

Polyclonal rat antisera directed against the 80 kDa protease were prepared by administration of 80 kDa protease which had been purified to homogeneity. The sera produced thereby immunoprecipitated the 80 kDa protease, but did not precipitate the 72 kDa protease or the 92 kDa protease. Hence, it was possible to differentiate the hormone-dependent malignancy producing 80 kDa from malignancies lacking this enzyme.

Immunizations are also conducted using immunogens which are cross-linked by incubating with 0.1% butaraldehyde for 30 minutes at 37° C. Excess glutaraldehyde is then quenched by adding 1/10 volume of 1M glycine, pH 7.4 followed by exhaustive dialysis for several days against 1% Triton X-100 in PBS.

Immunogens are also prepared by excising the 80 kDa bands from gel (Immobilon is an example of such a gel). The 80 kDa-containing band is then subjected to electrophoretic purification. The bands are pulverized in liquid nitrogen, then mixed with complete adjuvant and injected subcutaneously into the animals.

The animals are given boosters after two weeks. Three to four days after the booster injection, the sera containing polyclonal antibodies is collected and screened. Serum containing antibodies can be detected by Western-blot the 80 kDa protein, immunoprecipitating the 80 kDa protease activity as detected by gelatin zymography, and/or inhibiting the degradation of substrate by the in vitro ECM degradation assay. Hybridoma fusion processes are started immediately.

Activity of monoclonal and polyclonal antibodies against 80 kDa antigens can be tested by several means. Western blot is used for the initial screening using 80 kDa bands as electrophoretically transferred to nitrocellulose paper. This screening procedure selects for high affinity antibodies, since they must survive stringent washing methods. The monoclonal antibodies are used in screening the cDNA libraries. ELISA methodology can also be used as an alternate for initial screening.

Secondary screening is accomplished using immunofluorescence of cell antigens. The ScreenFAST apparatus used according to manufacturer's instructions is available from Life Technologies, Inc. and is particularly adapted for this purpose. The procedure makes it possible to rapidly screen up to 64 clones at a time while confirming the cell surface specificity of the antibody. This screening method makes it possible to do immunological localization. Clones that screen positive for both Western blotting and immunofluorescence are prime candidates for evaluation.

An antibody that is capable of immunoprecipitating an antigen can be purified for further characterization. The antigen is subjected to a gelatin zymogram for identification of protease activity. In vitro ECM degradation (ECM degradation) is used as a parallel screen for function-perturbing antibodies. The degradation of substrates coupled to crosslinked gelatin films by tumor cells is performed using breast cancer cells (50 μl) mixed with an equal amount of hybridoma conditioned medium (50 μl). This is added to prepared substrates to allow degradation of the film. Most cells required 6–18 hours for detectable degradation. As an alternative, breast cancer cells are added to each well of a 96-well microtiter plate that has been coated with 10 μg/μl biotin-fibronectin. After allowing the cells to grow for 18 hours, the cells are fixed, permealized, and analyzed with ELISA using goat anti-biotin antibody. Cells require only 18 hours for detectable degradation of biotin-fibronectin. The supernatants that show inhibition of the degradation process are further purified and the assay is repeated to avoid false responses from cytotoxic agents in the supernatants.

Monoclonal antibodies that inhibit the active site of the membrane proteases greatly facilitate studies on structure and function of these molecules. Their use provides the most stringent test for the function of the protease in vivo. There are presently available several panels of monoclonal antibodies directed against putative membrane proteases and their copurified proteins, including protease inhibitors.

Antibodies produced against the 80 kDa protease are useful for diagnostic and therapeutic applications for breast cancer. The use of blotting tests such as the Western blot make it possible to identify presence of 80 kDa enzyme in breast tissue after biopsy as a guide to further therapy. The antibodies may be used to block the effect of 80 kDa in the body to inhibit tumor growth and/or metastases. The dosage of any antibody will depend upon the condition, size and age of the patient. In determining 80 kDa inhibiting effective amount of any antibody, the level of expression of 80 kDa as determined by methods such as zymography and antigen/antibody interactions will be considered in determining dosage requirements. The antibodies may be humanized to improve patient tolerance.

Antibodies may also be linked to cytotoxic agents such as ricin A chain or B chain or abrin. Antibodies may be made bispecific, incorporating a secondary determinant reactive to cytotoxic lymphocytes in addition to tumor cells overexpressing the 80 kDa protease.

Antibodies may be radiolabelled to allow tumor localization and/or treatment.

We claim:

1. A matrix-degrading proteinase having an average molecular weight of about 80 kDa, purified to homogeneity, which is active in the presence of $Ca^2$, $Mg^2$ and $Mn^2$, is active over a pH range of 7.5 to 9.5, and degrades gelatin and type IV collagen.

2. A proteinase of claim 1 further comprising a support to which said proteinase is attached.

3. A proteinase of claim 2 wherein the support is a nitrocellulose strip.

4. A proteinase of claim 1 further comprising an antibody wherein said antibody is attached to said proteinase.

5. A proteinase of claim 4 further comprising a solid support which is attached to the antibody.

6. A composition comprising a proteinase of claim 1 in a pharmaceutically acceptable carrier, said composition having a pH within the range of 7.5 to 9.5.

* * * * *